(12) United States Patent
Colon

(10) Patent No.: US 10,105,197 B1
(45) Date of Patent: Oct. 23, 2018

(54) METHOD OF TREATMENT FOR PERIODONTAL POCKETS

(76) Inventor: Fernando Colon, New Albany, OH (US)

( * ) Notice: Subject to any disclaimer, the term of this patent is extended or adjusted under 35 U.S.C. 154(b) by 412 days.

(21) Appl. No.: 12/732,585

(22) Filed: Mar. 26, 2010

Related U.S. Application Data

(60) Provisional application No. 61/163,583, filed on Mar. 26, 2009.

(51) Int. Cl.
| | | |
|---|---|---|
| *A61C 8/00* | (2006.01) | |
| *A61K 6/00* | (2006.01) | |
| *C08L 67/00* | (2006.01) | |
| *A61K 9/16* | (2006.01) | |
| *A61K 31/22* | (2006.01) | |
| *A61K 31/047* | (2006.01) | |
| *A61K 9/00* | (2006.01) | |
| *A61K 31/075* | (2006.01) | |
| *A61K 9/10* | (2006.01) | |
| *A61C 8/02* | (2006.01) | |
| *A61K 9/19* | (2006.01) | |

(52) U.S. Cl.
CPC .......... *A61C 8/0006* (2013.01); *A61C 8/0016* (2013.01); *A61K 6/0038* (2013.01); *A61K 9/0024* (2013.01); *A61K 9/0063* (2013.01); *A61K 9/10* (2013.01); *A61K 9/1623* (2013.01); *A61K 9/1647* (2013.01); *A61K 9/1652* (2013.01); *A61K 31/047* (2013.01); *A61K 31/075* (2013.01); *A61K 31/22* (2013.01); *C08L 67/00* (2013.01); *A61K 9/19* (2013.01)

(58) Field of Classification Search
CPC ..... A61C 8/006; A61C 8/0006; A61C 8/0016; A61K 6/0038; A61K 9/0024; A61K 9/0063; A61K 9/10; A61K 9/1623; A61K 9/1647; A61K 9/1652; A61K 9/19; A61K 31/047; A61K 31/075; A61K 31/22; C08L 67/00
USPC ................................ 424/78.31, 78.08, 78.37
See application file for complete search history.

(56) References Cited

U.S. PATENT DOCUMENTS

| | | | | |
|---|---|---|---|---|
| 4,919,939 | A * | 4/1990 | Baker | 424/493 |
| 5,041,373 | A * | 8/1991 | Chambers | 435/7.9 |
| 5,324,520 | A * | 6/1994 | Dunn | A61B 5/02411 264/4.1 |
| 5,783,205 | A * | 7/1998 | Berggren et al. | 424/426 |
| 6,238,648 | B1 * | 5/2001 | Leusch et al. | 424/49 |
| 6,325,991 | B1 * | 12/2001 | Draheim | 424/49 |
| 6,716,251 | B1 | 4/2004 | Asius et al. | |
| 7,314,636 | B2 | 1/2008 | Caseres et al. | |
| 7,322,825 | B2 * | 1/2008 | Szymaitis | A61L 27/24 424/499 |

(Continued)

OTHER PUBLICATIONS

Ramfjord (The Periodontal Disease Index (PDI), Journal of Periodontology (1967) 38:602-609 (8 pages).*

(Continued)

*Primary Examiner* — Ernst V Arnold
*Assistant Examiner* — Miriam A Levin
(74) *Attorney, Agent, or Firm* — Yimei C. Hammond; Barrett, Easterday, Cunningham & Eselgroth

(57) ABSTRACT

A method of treating a periodontal pocket, comprising a step of administering one or more biodegradable compounds in a suitable carrier into the periodontal pocket, wherein the compound induces partial or total filling of the periodontal pocket for a period of time. Preferably, the biodegradable compound is Poly-L-lactic acid.

6 Claims, 2 Drawing Sheets

Injections technique to apply Poly-L-lactic acid into periodontal space:

Injections may be performed through
(1) the gingival tissue into the periodontium
(2) through the pocket itself.

(56) References Cited

U.S. PATENT DOCUMENTS

| | | | |
|---|---|---|---|
| 7,731,758 B2 | 6/2010 | Asius et al. | |
| 8,414,657 B2* | 4/2013 | Asius et al. | 623/23.75 |
| 2003/0199615 A1* | 10/2003 | Chaput et al. | 524/2 |
| 2004/0191323 A1* | 9/2004 | Asius et al. | 424/489 |
| 2006/0154210 A1* | 7/2006 | Martin et al. | 433/215 |

OTHER PUBLICATIONS

Meadows et al. (A Comparison of Polylactic Acid Granules and Decalcified Freeze-Dried Bone Allograft in Human Periodontal Osseous Defects, J. Periodontal (1993) 64 (2): 103-109), 7 pages.*

Teparat et al. (Clinical Comparison of Bioabsorbable Barriers With Non-Resorbable Barriers in Guided Tissue Regeneration in the Treatment of Human Intrabony Defects, J. Periodontol (1998) 69 (6): 632-641), 10 pages.*

American Academy of Cosmetic Dentistry, Cosmetic Procedures [Retrieved from internet <URL: http://www.aacd.com/index.php?module=cms&page=586 >] [Downloaded Apr. 19, 2015], 3 pages.*

American Academy of Cosmetic Dentistry, Periodontal Plastic Surgery [Retrieved from internet <URL: http://www.aacd.com/index.php?module=cms&page=578 >] [Downloaded Apr. 19, 2015], 3 pages.*

American Polymer Standards Corporation, Polylactic Acid Material Safety Data Sheet (last updated Jul. 7, 2008) [Retrieved from internet <URL: https://web.archibe.org/web/20090106174052/http://www.ampolymer.com/MSDS/PLA.pdf >], 2 pages (Year: 2008).*

Drugs.com, Sculptra (injectable poly-L-lactic acid) FDA Approval Histor—Drugs.com, [Retrieved from internet <URL: http://www.drugs.com/history/sculptra.html >], [Downloaded Sep. 16, 2014]), 1 page (Year: 2014).*

PubChem, lactic acid, [Retrieved from internet <URL: https://pubchem.ncbi.nlm.nih.gov/compound/lactic_acid#section=Top >], [Downloaded May 29, 2018], pp. 1-16 provided (Year: 2018).*

Unknown Individual Authors, Originating group—American Academy of Periodontology—Research, Science, and Therapy Committee, revised by Dr. Paul S. Rosen, Treatment of Plaque-Induced Gingivitis, Chronic Periodontitis, and Other Clinical Conditions, The American Academy of Periodontology reference manual, 2004, v30/No. 7, endorsements 253-262.

Unknown Individual Authors, prepared by the Research, Science and Therapy Committee of the American Academy of Periodontology, Treatment of Plaque-Induced Gingivitis, Chronic Periodontitis, and Other Clinical Conditions, J. Periodontol. 2001, pp. 1790-1800, vol. 72, n. 12.

Kaigler, D; Cirelli, JA; Giannobile, WV; Growth factor delivery for oral and periodontal tissue engineering; NIH Public Access Author Manuscript; 2008; pp. 1-20; public online, PMCID: PMC2573469.

Rotundra, AM; Narins, RS; Poly-L-lactic acid: a new dimension in soft tissue augmentation; 2006; pp. 151-158; Dermatologic Therapy, vol. 19.

Vesala, AL; Kallioinen, MJ; Kaarela, OI; Pohjonen, T; Tormala, PO; Waris, TJ; Poly-L-lactic acid plate for covering of small cranial bone holes: an experimental study in rabbits. 2000, pp. 36-38; Eur. J. Plast. Surg., vol. 23.

Alves, NM; Shi, J; Oramas, E; Santos, JL; Tomas, H; Mano, JF; Bioinspired superhydrophobic poly(L-lactic acid) surfaces control bone marrow derived cells adhesion and proliferation. 2008, pp. 480-488; Journal of Biomedical Materials Research Part A; Published online on www.interscience.wiley.com, DOI: 10.1002/jbm.a.32210.

Van Dijk, M; Van Diest, PJ; Smit, TH; Berkhof, H; Burger, EH; Wuisman, PIJM. Four-Year Follow-Up of Poly-L-lactic Acid Cages for Lumbar Interbody Fusion in Goats. 2005; pp. 125-138; Journal of Long-Term Effects of Medical Implants, vol. 15, No. 2.

Nygaard-Ostby, P; Bakke, V; Nesdal, O; Nilssen, HK; Susin, C; Wikesjo, Ume. Periodontal healing following reconstructive surgery: effect of guided tissue regeneration using a bioresorbable barrier device when combined with autogenous bone grafting. A randomized controlled clinical trial. 2008; pp. 37-43; Journal of Clinical Periodontology, vol. 35, doi: 10.1111/j.1600-051X.2007.01160.x.

Reynolds, MA; Aichelmann-Reidy, ME; Branch-Mays, GL; Gunsolley, JC. The Efficacy of Bone Replacement Grafts in the Treatment of Periodontal Osseous Defects. A Systematic Review. 2003; pp. 227-265; Ann. Periodontol., vol. 8, No. 1.

Fitzgerald et al., "Facial vol. restoration of the aging face with poly-l-lactic acid" Dermatologic Therapy (2011) vol. 24, pp. 2-27.

Sculptra Aesthetic marketing material ("stimulates collagen for a natural look") published by Valeant (2012), 6 pages.

Sculptra presentation to the FDA on Mar. 25, 2004 ("Sculptra—P030050"), 25 pages.

Sculptra prescribing information as of Sep. 2009, 24 pages.

Sculptra Aesthetic prescribing information as of May 2012, 11 pages.

* cited by examiner

Injections technique to apply Poly-L-lactic acid into periodontal space:

Injections may be performed through
(1) the gingival tissue into the periodontium
(2) through the pocket itself.

METHOD OF TREATMENT FOR PERIODONTAL POCKETS

CROSS-REFERENCES TO RELATED APPLICATIONS

This application claims the benefits of U.S. Provisional Application 61/163,583 filed on Mar. 26, 2009. The contents of the provisional application are incorporated herein by reference.

STATEMENT REGARDING FEDERALLY-SPONSORED RESEARCH AND DEVELOPMENT (Not Applicable)

REFERENCE TO AN APPENDIX (Not Applicable)

BACKGROUND OF THE INVENTION

1. Field of the Invention

This invention relates generally to a process of treating periodontal pockets or cavities.

2. Description of the Related Art

Periodontal disease is an all-inclusive term for a variety of clinical conditions that are forms of either gingivitis or periodontitis. Gingivitis is an inflammation of the gingiva (or gums) that can be associated with poor oral hygiene and/or the hormonal state of the patient. It is believed that gingivitis, if untreated, will develop into periodontitis. Periodontitis is a bacterial disease in which the infection has progressed to affect or destroy the oral tissues and bones which retain and support the teeth in the jaw and maxillary bones. Periodontitis, if untreated, will eventually result in the loss of the affected teeth.

Chronic periodontitis is characterized by the inflammation and loss of soft tissues and bone at the periodontium, which creates a periodontal "pocket" or cavity. This pocket serves as a nest for recurring bouts of infection that cause further deepening of the pocket. Most of these infections are caused by periodontal pathogens. Periodontal pathogens generate endotoxins, which stimulate several osteoclast-related mediators to target the destruction of alveolar bone (the bone supporting the teeth) and supporting connective tissue such as the periodontal ligament.

Although dental cavities may be effectively treated with a combination of proper hygiene and fluoride, periodontal disease is often more difficult to treat. This difference in amenability to treatment reflects by the markedly different environments of the oral and periodontal pockets. The oral cavity is essentially an aerobic environment, which is constantly perfused by saliva. In contrast, the periodontal microenvironment is more anaerobic and is perfused by a plasma filtrate, known as the "crevicular fluid." The growth of microorganisms within this microenvironment may cause periodontal disease. Hence, the treatment of the disease is directed toward controlling this growth. As the periodontal disease becomes more established, the periodontal microenvironment becomes more anaerobic and the flow of crevicular fluid increases.

Efforts to treat periodontal disease have been impeded by several factors. Because the site of the bacterial infection is largely inaccessible to agents present in the periodontal pocket, antimicrobial agents provided to the pocket such as, for example, in a mouth wash are generally ineffective. The increased outward flow of crevicular fluid, which accompanies periodontal disease, has the effect of preventing therapeutic agents placed within the periodontal pocket from entering the site of the bacterial infection.

The current treatments for periodontal pockets focus on controlling the progression of the pocket (preferably obtaining reduction of the pocket depth), healing and preserving the tooth. These treatments include aggressive hygiene, lifestyle changes such as smoking cessation, scaling and probing of the pocket, gum trimming and surgery with or without flaps and bone grafts. All of these treatments aim to obtain tissue and/or bone regeneration.

Most recently, efforts have been directed towards guided genetic tissue regeneration and/or guided bone regeneration. The purpose of tissue and bone regeneration techniques is to develop and/or restore the tooth-supporting structures, which include bones, ligaments and tissues. Recent studies have confirmed that growth factors can improve the capacity of tissues to generate, improving cellular chemoattraction, differentiation and proliferation. Growth factors are natural biological mediators that regulate important cellular events involved in tissue repair by binding to specific cell surface receptors. The effect of each growth factor is regulated through a complex system of feedback loops that involve other growth factors, enzymes and binding proteins.

The concepts of guided tissue regeneration (GTR) and guided bone regeneration (collectively called the regenerative treatment) aim to optimize the environment in which cells and tissues grow. In other words, the regeneration techniques involve a study of methods of delivering growth factors into the periodontal pockets to promote the regeneration of tissue/bone cells. One method is using different membranes as barriers, which support the ingrowth of more favorable tissue regenerative cells (i.e., periodontal ligament (PDL) cells, bone cells), while selectively excluding non-desirable cells (i.e., gingival epithelial cells, connective tissue cells) from the reconstruction sites. Further, these barrier membranes also support the establishment of other critical parameters to successful periodontal regeneration: tenting and isolation (the barrier membrane adapts to ensure adequate space will be maintained for tissue regeneration); scaffolding (the barrier membrane serves as a matrix-enabling organization of tissue progenitor cells and newly formed vasculature); and stabilization (the barrier membrane protects the area from being mobilized during initial phases of healing and regeneration).

Two common types of polymeric material used in forming barrier membranes, or in growth factor delivery strategies, are natural collagen-derived materials and synthetic polymers of lactic and glycolic acid (i.e., poly[lactic-co-glycolide]). Barrier membranes derived from natural compounds (i.e., collagen) are degraded by an enzymatic process (biodegration), and catalyzed by cells in the local microenvironment and within the developing tissue. However, synthetic polymers (i.e., derivatives of poly-lactic and poly-glycolic acid) are hydrolyzed (bioabsorption) into the natural metabolites lactic acid and glycolic acid.

In treating periodontal pockets, the regenerative treatment has been a challenge due to morphological and functional specificities of each component of tooth-supporting bones and tissues. Supporting tissues are known as the periodontium, which includes the gingiva (gums), alveolar bone, cementum, and the periodontal ligament. Further, some limitations exist with respect to bone volume, safety and predictability of existing growth factor delivery methods. In sum, although the regenerative treatment shows some promise of treating periodontal pockets, the regenerative treatment is very complex, unpredictable and costly.

BRIEF SUMMARY OF THE INVENTION

This invention provides a simpler, cost-effective, non-surgical technique to treat periodontal pockets in order to prevent progressive deepening of the pockets.

Broadly, the present invention is a method of treating a periodontal pocket, comprising the steps of (a) cleaning the periodontal pocket; and (b) administering a mixture comprising one or more biodegradable or biocompatible compounds in a suitable carrier into the periodontal pocket, wherein the compound induces a partial or total filling of the periodontal pocket for a period of time. Preferably, the periodontal pocket suitable for using the method in the present invention should have a depth of about 5 mm or deeper.

Preferably, the biodegradable compound in a suitable carrier is administered through an injection through the gingival tissue into the periodontium or through the pocket into the periodontium. The partial/total filling of the pocket may last for a period of time in the range of 2 weeks to 12 months, depending on the initial depth of the pocket.

For some embodiments of the present invention, the biodegradable compound comprises polymer of lactic acid repeat units, collagen, hyaluronic acid, hydroxylapatite, polymethylmethacrylate, or a mixture thereof. Preferably, the biodegradable compound is Poly-L-lactic acid.

For some embodiments, the suitable carrier comprises a pharmaceutically acceptable carrier. Unlimited examples of the pharmaceutically acceptable carrier include water, saline, starch, hydrogel, polyvinylpyrrolidone, polysaccharide, hyaluronic acid ester, or plasma.

For some embodiments, the suitable carrier may also contain a suspending agent. Suitable suspending agents include, but are not limited to, a cellulose derivative or a pharmaceutically acceptable acid or ester. Preferably, the cellulose derivative may be hydroxypropylmethylcellulose or carboxymethylcellulose.

For some embodiments, the suitable carrier further contains a cryoprotecting agent. Suitable cryoprotecting agents include, but are not limited to, d-mannitol, lactose, sucrose, fructose, a sugar, a carbohydrate, or dextran.

For some embodiments, the suitable carrier may also contain a medicament. Unlimited example of the medicament is an anesthetic, an antibiotic, a steroid, an analgesic, an antiseptic, or a combination thereof.

For some embodiments, after administration of the biodegradable compound, it is desirable to maintain the cleanness of the periodontal pocket, which comprises irrigation with warm water and/or warm salt water.

In a further embodiment, if needed, the biodegradable compound can be re-administered to the periodontal pocket after a period of time in the range of 2 weeks to about 8 weeks until the periodontal pocket is shown to be clinically improved and stable. Preferably, the depth of the periodontal pocket is reduced to 3-5 mm or less.

For some embodiment of the method, after the pocket is shown to be clinically stable (preferably the pocket depth is reduced to 3-5 mm or less), the pocket can be maintained by re-administering the biodegradable compound after a period of time, wherein the period of time is in the range of 3 months to about 12 months.

Alternatively, the present invention is a method of treating a periodontal pocket, comprising:
   a. cleaning the periodontal pocket;
   b. administering one or more biodegradable or biocompatible compounds in a suitable carrier into the periodontal pocket, wherein the compound induces a partial or total filling of the periodontal pocket for a period of time;
   c. re-administrating the biodegradable compound after a period of time, wherein the period of time is in the range of about 3 weeks to about 6 weeks; and
   d. repeating step c until the periodontal pocket is shown to be clinically improved and stable.

Preferably, the biodegradable compound is Poly-L-lactic acid, and the periodontal pocket has a depth of at least 5 mm before the treatment by the present invention.

For some embodiments, the suitable carrier comprises water, carboxymethylcellulose, mannitol, and a mixture thereof. The suitable carrier may also contain anesthetics, such as lidocaine.

Preferably, the administration of the Poly-L-lactic acid is accomplished by injecting the Poly-L-lactic acid into the periodontium either through gingival tissues or through the pocket.

For some embodiments, after the periodontal pocket is shown to be clinically improved and stable, the pocket is maintained by re-administering the Poly-L-lactic acid into the periodontium every 3 to 12 month if needed to control the progression of the periodontal pocket.

Embodiments of the invention address some or all of the concerns discussed above. This brief summary has been provided so that the nature of the invention may be understood quickly. A more complete understanding of the invention may be obtained by reference to the following description of the preferred embodiments thereof in connection with the attached drawings.

Figure 1:
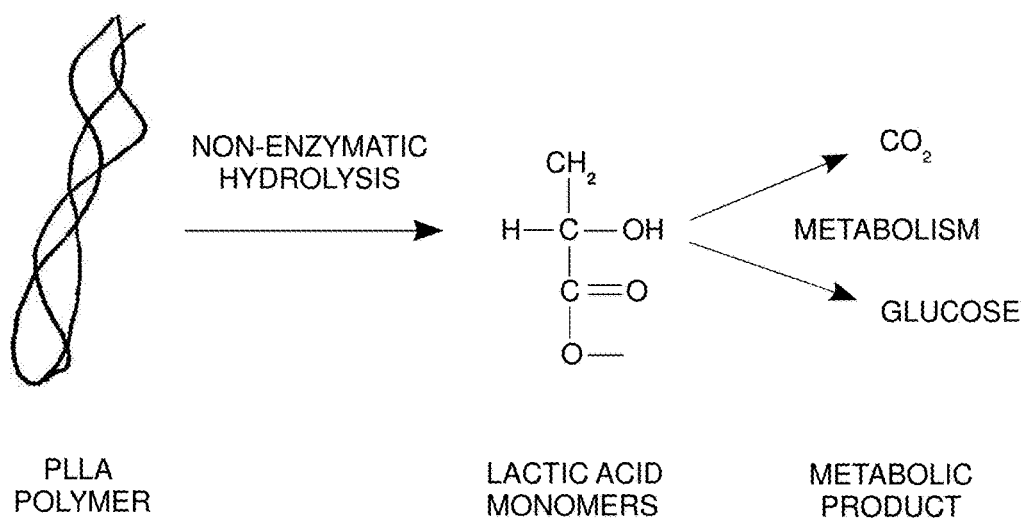
FIG. 1 is an illustration of a metabolic pathway for degradation of poly-1-lactic acid (PLLA) (Rotunda, A. M.; Narins, R. S.; 2006, Dermatologic Therapy, vol. 19, pp. 151-158).

In describing the preferred embodiment of the invention which is illustrated, for example, in the drawings, specific terminology will be resorted to for the sake of clarity. However, it is not intended that the invention be limited to the specific term so selected and it is to be understood that each specific term includes all technical equivalents which operate in a similar manner to accomplish a similar purpose. For example, the words connected or terms similar thereto are often used.

DETAILED DESCRIPTION OF THE INVENTION

Broadly, this invention is a method of treating a periodontal pocket by inducing a temporary partial or complete filling of the pocket. It involves (a) administrating a biodegradable compound into a cleaned periodontal pocket, which induces a temporary partial or complete filling of the pocket, and (b)

maintaining the cleanness of the pocket through proper oral hygiene, such as irrigation with warm water and gentle flossing.

Re-administration of the biodegradable compound into the previously treated pocket might be needed after about 2 weeks or about 8 weeks until the periodontal pocket is shown to be clinically improved and stable. The clinical improvement and stableness are demonstrated by the lack of inflammation and the lack of the progression of the periodontal pocket. Preferably, the improvement is shown by reducing the depth of the periodontal pocket to about 3-5 mm or less and a good clinical appearance of the pocket. Some pockets may not reach the optimal 3 mm depth, however the clinical benefits will still be evident to any treating physician or dentist. Then, the pocket may be maintained by administration of the compound to the pocket after about 3 to 12 months.

Figure 2:
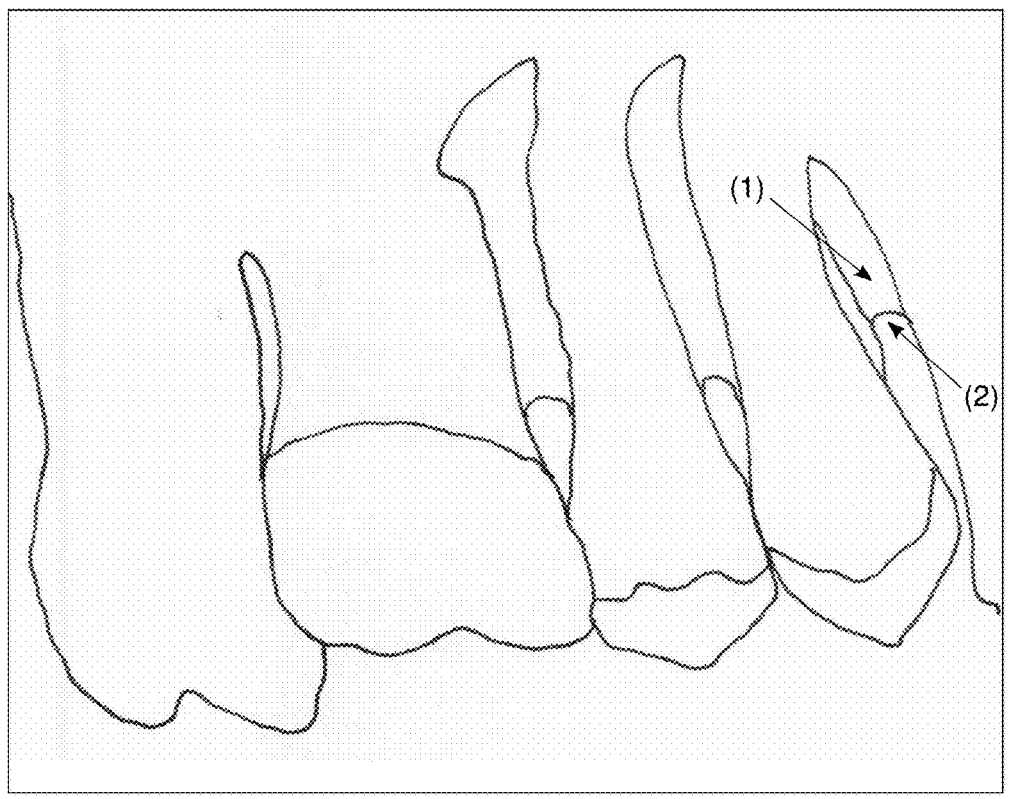
FIG. 2 is an illustration of injection sites for the administration of PLLA into the periodontal pocket as performed in the Example.

A preferred method of administering the compound into the periodontal pocket is to inject a solution/suspension of the compound into the existing periodontal surface tissues of the pocket (the periodontium) as shown by FIG. 2.

The biodegradable compound used must have proper mechanical properties to comply with the objective of inducing moderate filling of the periodontal pocket. They should not have toxic effects and are preferably substantially metabolized upon degradation.

For some preferred embodiments of the present invention, the biodegradable compounds are administered through injection. Injectables of the biodegradable compounds can be present in various physical forms, including both activated form (i.e., ready for administration) and pre-activated form (i.e., requiring additional manipulation or processing prior to administration).

The activated form is typically a suspension of the polymeric particles of the biodegradable compound in a suitable carrier, preferably a pharmaceutically acceptable carrier. Examples of pharmaceutical carriers include but are not limited to water, saline, starch, hydrogel, polyvinylpyrrolidone, polysaccharide, hyaluronic acid ester, or plasma, with water being the preferred carrier. The pre-activated form is typically a dried powder packing in the pharmaceutically acceptable carrier and/or one or more other ingredients that are soluble in the pharmaceutical acceptable carrier (such as the buffering agent(s), cryoprotecting agent, suspending/gelling agent, surfactant, medicament, anesthetic, etc.) As used herein, a suitable carrier includes a suitable pharmaceutical carrier and other ingredients that are soluble in the pharmaceutical acceptable carrier.

The injectable of the present invention may be provided in a ready for use prefilled sterile syringe, or in a vial in the form of a sterile suspension. In preferred embodiments, the injectable may be in the form of a lyophilized powder, such as Sculptra®, to facilitate sterilization and storage. In these preferred embodiments, before administration, the end user adds water or other pharmaceutically acceptable carriers and/or additional components prior to injection. The injectable may also be provided in a two-component prefilled syringe, one containing the freeze-dried powder and the other containing water or other pharmaceutical acceptable carrier.

The particles of the biodegradable compound that may be employed in the injectables of the biodegradable compound typically are prepared by processing the particles to an appropriate size and/or shape. Preferably, the shape of the particles is substantially spherical.

For some embodiments, the injectables may be administered as a relatively homogenous suspension of the particles.

To achieve that end, the suitable carriers may contain a suspending agent and/or a gelling agent. Suitable suspending agent or gelling agents include, but are not limited to, cellulose derivates, such as hydroxypropylmethylcelulose (HPMC) and carboxymethylcellulose (CMC), synthetic hyaluronic acids, lactic acid esters, sodium carmellose, caproic acid esters, and the like, with CMC being preferred. The concentration of the suspending agent/gelling agent in the activated form may typically vary in the range of about 0% to about 10% by weight.

For some embodiments, the suitable carrier for the compound may also contain a cryoprotecting agent. A cryoprotecting agent is a chemical which prohibits or reduces the formation of damaging ice crystals in biological tissue during cooling. Suitable cryoprotecting agents include, but are not limited to, sugars and carbohydrate, such as d-mannitol, mannitol, lactose, sucrose, fructose, and dextran, with mannitol being preferred. The concentration of the cryoprotecting agent may be in the range of about 0% to about 45% by weight.

For some embodiments, the injectable of the biodegradable compound may also contain a medicament. As used herein, a "medicament" may be any bioactive composition, pharmaceutical, drug or compound which one desires to administer to the site of the injection of the biodegradable compound. For example, the medicament may include an anesthetic to decrease the pain or discomfort associated with injecting the compound that facilitates the integration of the polymer or decreases the trauma to the injection site. Exemplary anesthetics include, but are not limited to, lidocaine, xylocaine, novocaine, benzocaine, prilocaine, ripivacaine, and propofol. Other examples of the medicament include an antibiotic, a steroid, an analgesic, an antiseptic, or a combination thereof.

The biodegradable compound suitable for this invention includes, but is not limited to, polymers of lactic acid repeat units (preferably Poly-L-lactic acid), collagen, hyaluronic acid, hydroxylapatite, polymethylmethacrylate, and a mixture thereof. Preferably, the biodegradable compound is injectable. More preferably, the biodegradable compound is hydroxylapatite, or Poly-L-lactic acid. Most preferably, the biodegradable compound is Poly-L-lactic acid (PLLA).

Collagen is a natural protein that supports the skin. Preferably, injectable collagen formula are derived from human dermis include Cosmoderm® or Cosmoplast®. A less preferred version of injectable collagen is bovine collagen, which unlike human derived collagen, requires prior allergy testing. Hyaluronic acid is a natural substance found in human bodies. It is well suited to plump thin lips and to fill facial creases such as nasolabial folds. It may also be appropriate for some surface wrinkles and concave scars. Hydroxylapatite is a mineral-like compound found naturally in human bones, suspended in a gel-like formulation. Polymethylmethacrylate (PMMA) contains 20% PMMA microspheres suspended in 80% purified collagen gel.

Poly-L-lactic acid (PLLA) is a biodegradable, biocompatible, and bio-absorbable polymer that has been used widely in medical literature. Currently, it is used as a temporary filler to treat facial lines for cosmetic purposes, such as wrinkles and soft tissue regularities. In treating periodontal pockets, poly-lactic acid (not just Poly-L-lactic acid) is used as a carrier, such as barrier membrane and scaffolds, or as an adjuvant to open flap and bone grafting operations.

PLLAs are metabolized along a similar metallic pathway as lactate/pyruvate as shown by FIG. 1. Injection of PLLA into the subcutaneous tissue causes a biological response that is similar but less inflammatory than what is seen after suture reactions and wound repair. PLLA is considered biodegradable because it disappears after injection as a result of enzymatic and non-enzymatic hydrolysis. Specifically, as shown by FIG. 1, PLLA hydrolyzes over time into lactic acid monomers; lactic acid monomers are then converted to pyruvate, which is ultimately converted into carbon dioxide and water via the tricarboxylic acid (Krebs, Citric) cycle. Accordingly, there is a natural transition from acute inflammation into low-grade chronic inflammation over time. The precise mechanism of action that produces the filling effects of injected PLLA has not been fully elucidated, but it appears to be related to the host's response and gradual degradation of the material. It is believed that the filling effect of the injected PLLA might be due to a combination of several factors, such as foreign body inflammatory response, dermal fibroplasias, and slow PLLA microsphere degradation.

Preferably, a suspension/solution of PLLA in a suitable carrier is injected into the depth of the gingival and/or existing periodontal tissue layer of the periodontal pocket. Suitable carriers include, but are not limited to, biodegradable excipients, sterile water, or a mixture thereof. Unlimited examples of biodegradable excipients are suspending agents, cryoprotective agents, and mixtures thereof. Sterile water is also called bacteriostatic water suitable for injection.

Injectable PLLA are commercially available in the form of NewFill™ and Sculptra®, both which are consisted of dried microparticles of PLLA along with sodium carboxymethylcellulose (a suspending agent that aids water dispersion), and pyrogen-free mannitol (a cryoprotective agent). The excipients, sodium carboxymethylcellulose and mannitol, are biodegradable. One vial of the PLLA microparticles is reconstituted by slow addition of 3-13 cc of sterile water suitable for injection, and an optional addition of 2 cc of 1% lidocaine.

Sculptra® is an injectable implant containing microparticles of poly-L-lactic acid (PLLA) (a biocompatible, biodegradable, synthetic polymer from the alpha-hydroxyacid family), carboxymethylcellulose (USP), nonpyrogenic mannitol (USP) and sterile water for injection (USP). Sculptra® is available as 367.5 mg dose vials and is reconstituted prior to use. Sculptra® (injectable poly-L-lactic acid) is manufactured by Dermik Laboratories, a business of Sanofi-Aventis U.S. LLC. The PLLA particles in Sculptra® are irregular shaped microparticles.

In the present invention, the PLLA can be injected into the periodontal pocket by a needle. As shown in FIG. 2, the needle is inserted 1-3 cc of the prepared PLLA suspension/solution into the periodontium through gingival tissue or through the pocket itself. Preferably, the PLLA is injected into the gingival and/or existing periodontal tissue layer of the periodontal pocket so as to induce the temporary filling effect of the pocket. To prevent any blockage of PLLA crystals, a minimum size of 25 gauge needle is preferred.

After injection, in addition to good oral hygiene practice, the cleanness of the periodontal pocket must be maintained by irrigation with warm water or warm salt water with or without a mild antiseptic for 2-3 times per day and after each meal. Good oral hygiene practices suitable for the present invention include gentle flossing, brushing, etc. After the first week of the injection, irrigations may be done in the morning and evening only.

Repeat injections of the PLLA suspension every 2 to 8 weeks are recommended until the pocket has shown clinical improvement and stableness. The clinical improvement and stableness are demonstrated by the lack of inflammation and the progression of the periodontal pocket. Preferably, the clinical improvement and stableness is shown by the fact that the depth of the periodontal pocket is reduced to about 3-5 mm or less and a good clinical appearance of the pocket. Preferably, the repeat injection can be done every 4 to 6 weeks. After the periodontal pocket is shown to be clinically improved and stable, the injection may be discontinued. More preferably, the periodontal pocket should be re-evaluated after every 3 to 12 months, and then if needed, the biodegradable compound can be re-administered to prevent the periodontal pocket progression.

It is theorized that although PLLA would not create a permanent filling of the periodontal pocket, it can create a temporary filling of the periodontal pocket. Temporary filling of the pocket will reduce the depth of the pocket, making the pocket easier to clean, and thus, making the pocket less of a haven for bacteria and/or virus. This not only prevents deepening of the periodontal pocket due to continued infection by periodontal pathogens, it also improves the chances of local tissue growth. It is believed that the injection of PLLA creates a minimum disturbance of blood supply to the already compromised periodontium in a periodontal pocket. Open surgical procedures, such as grafting or insertion of synthetic filler, cause heavier damage to the periodontium's blood supply. As the result, the PLLA will not only induce a temporary filling of the pocket, it will also promote natural tissue growth, reducing the possibility of pathogen infection, all of which resulted in preventing periodontal pocket progression and preserving the tooth.

This temporary filling of the periodontal pocket by the injection of the PLLA is a surprising result because of the physiology of the pocket and the periodontal microenvironment. First, the PLLA is currently used to fill facial wrinkles, which are mostly surrounded by soft tissues with plenty of blood supply. Even before the existence of a periodontal pocket, the periodontium (the supporting tissue) does not contain much of soft tissue. Periodontium includes the gingiva (gums—mucosal tissue), alveolar bone, cementum (calcified substance covering the root of a tooth), and periodontal ligament. Periodontal pockets are characterized by a severe loss of the integrity of the periodontal tissues and bones. So within the periodontal pocket, there is a several reduction/compromise of the normal blood supply needed to assist in building the collagen for the filling of the pocket.

Second, when using the PLLA to fill the wrinkles on the face, the user can ensure the PLLA being injected into subcutaneous tissue in the wrinkle area. The injection of the PLLA into the periodontal pocket cannot be as controlled as that in the facial area because the pocket is very narrow and deep with significant tissue tightness. So the injection will aim to go through the gingival tissues into the periodontium or through the pocket into the periodontium.

Third, the periodontal pocket is perfused by a plasma filtrate, known as the "crevicular fluid." The increased outward flow of crevicular fluid has the effect of preventing any therapeutic agents placed within the pocket from really entering the periodontal pocket and affecting therapeutic changes. Therefore, the PLLA should not be injected into the pocket but into the periodontium. Otherwise, solutions inside the pocket may be pushed out by the crevicular fluid without creating any filling effects. It seems that the present invention is able to resolve these problems to ensure that the PLLA remains in the local tissues of the periodontium to induce temporary filling of the pocket.

For some preferred embodiments of the present invention, when administrating the PLLA to the periodontium, the following general principles or process should be followed:

1) The periodontal pocket must be cleaned so that the pocket has no active infection at time of the PLLA administration. A balanced bacterial flora is considered adequate. Any general acceptable dental cleaning procedure, including scaling of the pocket etc, can be performed to get rid of any existing periodontal pathogens. Such cleaning can be performed immediately prior to the administration of the PLLA or a couple days before the administration so long as the pocket is free of any active infection at the time of the PLLA administration.

2) The periodontal pocket suitable for the methods of the present invention should be deeper than 5 mm and should show no signs of improvement by traditional methods of treatments, such as scaling.

3) Administer 1 to 3 cc of the suspension/solution of PLLA directly into the pocket through the gingival tissues and/or the space the pocket itself.

4) Following the administration of the PLLA, the pocket must be maintained clean with the use of an irrigation device. The pocket must be irrigated with warm water (or warm salt water) with or without a mild antiseptic. For the first week, the irrigation must be done approximately three times a day and after each meal. Gentle flossing may be resumed after twenty four hours. After the first week, the irrigation may be done twice, once in the morning and once in the evening.

5) Perform clinical evaluation of the periodontal pocket after two to eight weeks, preferably after four to six weeks. Re-administer the PLLA to the periodontium if needed. Note: deep probing should be avoided until the new tissue has complete maturation. Early disturbance of the new tissue growth may interfere with the healing process. Limited probing may be required if deemed necessary by the treating physician during steps 4-6.

6) Repeat step 5 until the pocket has shown clinical improvement and stableness, preferably the pocket has shown an adequate depth reduction (a depth of 3-5 mm or less depending on the initial pocket depth) and a good clinical appearance. Then the administration of the PLLA may be discontinued, and routine hygiene may resume.

7) Re-evaluate the periodontal pocket at a time interval in the range of 6 to 12 months as needed. The administration (injection) of PLLA may be repeated when the signs of periodontal pocket progression or tissue resorption are noted.

The following examples are illustrative of the invention and are not meant to limit the scope of the invention in any way.

EXAMPLE

A 15 cc injectable suspension/solution of poly-L-lactic acid was prepared by mixing 367.5 mg of Sculptra® with 13 cc of bacteriostatic water and 2 cc of 1% lidocaine. Sculptra® is a registered trademark of Valeant Pharmaceuticals International, Inc.

Qualified periodontal pockets: A chronic periodontal deep pocket on tooth number 5 of a non-smoking adult male showed continuous deepening despite aggressive hygiene and scaling in an every three months program. The pocket surrounding the tooth was measured to be 7 mm-DL (distal lingual), 10 mm-L (lingual), 10 mm-ML (mesiolingual) and 7 mm/MB (mesiobuccal) on Dec. 3, 2008. Tooth fixation was good. An X-ray documenting the soft tissue and bone loss was obtained on Dec. 3, 2008.

On Jan. 8, 2009, the pocket was injected with 1 cc of the prepared injectable suspension/solution of Poly-L-lactic acid. The injection site is shown by FIG. 2 to be either through the gingival tissue into the periodontium or through the pocket itself into the periodontium. The pocket hygiene was maintained by irrigation with warm water at 3 times a day for the first week. After 24 hours, there was minimal local inflammation and discomfort. Conservative flossing of the area was started after 24 hours.

On Feb. 26, 2009, the same dentist performed a clinical re-evaluation of the treated periodontal pocket. He observed some improvements to the clinical appearance and some reduction to the depth of the pocket. An X-ray suggested an early filling of the space. A second dose of 1 cc of the Poly-L-lactic acid solution was injected into the periodontum.

On Mar. 11, 2009, the patient's periodontist reevaluated the pocket, who was unaware that the previous injections. The periodontist observed some clinical improvement of the periodontal pocket by the pocket appearance and by the pocket depth reduction to 2 mm-DL, 4 mm-L, 5 mm-ML and a maximum of 7 mm at MB. X-rays documenting the filling of the pocket with connective tissue were obtained.

A third dose of the injectable solution of Poly-L-lactic acid was done on Mar. 24, 2009. After the third injection, the treated periodontal pocket remained clinically stable, and the pocket depth was slightly reduced. The administration was discontinued.

Six months later, the pocket was observed to have shown some resorption of the temporary tissue filler, that is, the progression of the periodontal pocket depth. The PLLA suspension was re-administered to maintain the pocket so as to prevent the pocket depth progression.

This Example has shown that injection of PLLA to the periodontal pocket was successful in treating the pocket by reducing the pocket depth and preventing its progression. The injection of the PLLA was successfully accomplished by injecting it either through the gingival tissues into the periodontium or through the pocket itself into the periodontium as shown in FIG. 2. The PLLA remained to induce the partial or total filling of the patient's periodontal pocket for a temporary period of time. Repeat injections of the PLLA at 3 to 6 week intervals are recommended for at least 2 to 4 times until the pocket has shown clinical improvement and stableness by a qualified periodontist. Preferably, after repeat injection of the PLLA, the pocket depth is reduced to 3-5 mm or less and has a good clinical appearance. Thereafter, re-evaluation of the pocket, or re-administration of the PLLA if needed, should be performed at a 3 month to 12 month interval.

This detailed description in connection with the drawings is intended principally as a description of the presently preferred embodiments of the invention, and is not intended to represent the only form in which the present invention may be constructed or utilized. The description sets forth the designs, functions, means, and methods of implementing the invention in connection with the illustrated embodiments. It is to be understood, however, that the same or equivalent functions and features may be accomplished by different embodiments that are also intended to be encompassed within the spirit and scope of the invention and that various modifications may be adopted without departing from the invention or scope of the following claims.

The invention claimed is:

1. A method of reducing the pocket depth of a periodontal pocket comprising injecting into the periodontium of the periodontal pocket a solution/suspension comprising biodegradable poly-L-Lactic acid, sodium carboxymethylcellulose, d-mannitol and water; wherein the periodontal pocket has a depth of at least 5 mm before the administration of the solution/suspension; and wherein the poly-L-lactic acid induces a partial or a total filling of the periodontal pocket after at least one injection so as to reduce the pocket depth.

2. The method according to claim 1, wherein the periodontal pocket is cleaned according to usual dental practice prior to administration of an effective amount of poly-L-lactic acid.

3. The method according to claim 1, wherein the poly-L-lactic acid is administered by injection at one or more sites in the periodontium of the periodontal pocket.

4. The method according to claim 1, wherein the solution/suspension administered into the periodontium of the periodontal pocket has a volume of 1 to 3 cc.

5. The method according to claim 1, wherein the solution/suspension administered into the periodontium of the periodontal pocket has a volume of from 1 cc to 3 cc and is administered in a single injection.

6. A method of treating a periodontal pocket comprising:
Injecting a solution/suspension comprising an effective amount of poly-L-lactic acid into the periodontium of the periodontal pocket;
wherein the solution/suspension comprises poly-L-lactic acid, sodium carboxymethylcellulose, d-mannitol and water; wherein the periodontal pocket has a depth of about 5 mm or greater; and wherein the pocket depth of the periodontal pocket is reduced.

* * * * *